(12) United States Patent
Geczy

(10) Patent No.: US 7,767,227 B2
(45) Date of Patent: Aug. 3, 2010

(54) GALENICAL FORM FOR ORAL ADMINISTRATION WITH PROLONGED RELEASE OF MOLSIDOMINE

(75) Inventor: Jozsef-Michel Geczy, Brussels (BE)

(73) Assignee: Therabel Pharmaceuticals Limited, Galway (IE)

( * ) Notice: Subject to any disclaimer, the term of this patent is extended or adjusted under 35 U.S.C. 154(b) by 1544 days.

(21) Appl. No.: 10/182,718

(22) PCT Filed: Feb. 22, 2001

(86) PCT No.: PCT/EP01/02055

§ 371 (c)(1),
(2), (4) Date: Oct. 2, 2002

(87) PCT Pub. No.: WO01/62256

PCT Pub. Date: Aug. 30, 2001

(65) Prior Publication Data

US 2003/0045522 A1 Mar. 6, 2003

(30) Foreign Application Priority Data

Feb. 24, 2000 (FR) .................................. 00 02307

(51) Int. Cl.
*A61K 9/22* (2006.01)
*A61K 9/26* (2006.01)
*A61K 9/20* (2006.01)
(52) U.S. Cl. ...................... 424/468; 424/469; 424/470; 424/472; 424/465
(58) Field of Classification Search ................ 424/468, 424/469, 470, 472, 465, 467
See application file for complete search history.

(56) References Cited

U.S. PATENT DOCUMENTS

| 5,403,840 A | * | 4/1995 | Vikmon et al. | ............ 514/236.2 |
| 5,962,013 A | * | 10/1999 | Wong et al. | ................. 424/448 |
| 6,068,854 A | * | 5/2000 | Wunderlich et al. | ......... 424/464 |
| 6,426,087 B1 | * | 7/2002 | Saslawski et al. | ........... 424/450 |

FOREIGN PATENT DOCUMENTS

| EP | 624370 | 11/1994 |
| EP | 714661 | 6/1996 |
| WO | 91/14680 | 10/1991 |

* cited by examiner

*Primary Examiner*—Michael G Hartley
*Assistant Examiner*—Nabila G Ebrahim
(74) *Attorney, Agent, or Firm*—Dennison, Schultz & MacDonald

(57) ABSTRACT

The present invention relates to a novel sustained-release oral galenical form of molsidomine for the treatment of all forms of angina attack (angina of effort, spastic angina, mixed angina). According to the invention, this novel galenical form contains a therapeutically effective amount of molsidomine or one of its active metabolites and has an in vitro dissolution rate [measured spectrophotometrically at 286 or 311 nm by the method described in the European Pharmacopoeia, 3rd edition (or USP XXIV), at 50 rpm, in 500 ml of a 0.1 N HCl medium, at 37° C.] of: 15 to 25% of molsidomine released after 1 hour, 20 to 35% of molsidomine released after 2 hours, 50 to 65% of molsidomine released after 6 hours, 75 to 95% of molsidomine released after 12 hours, >85% of molsidomine released after 18 hours and >90% of molsidomine released after 24 hours, the plasma peak of molsidomine obtained in vivo occurring 2.5 to 5 hours, preferably 3 to 4 hours, following the administration of said form, and having a value of between 25 and 40 ng/ml of plasma. Application: therapeutics industry.

17 Claims, 5 Drawing Sheets

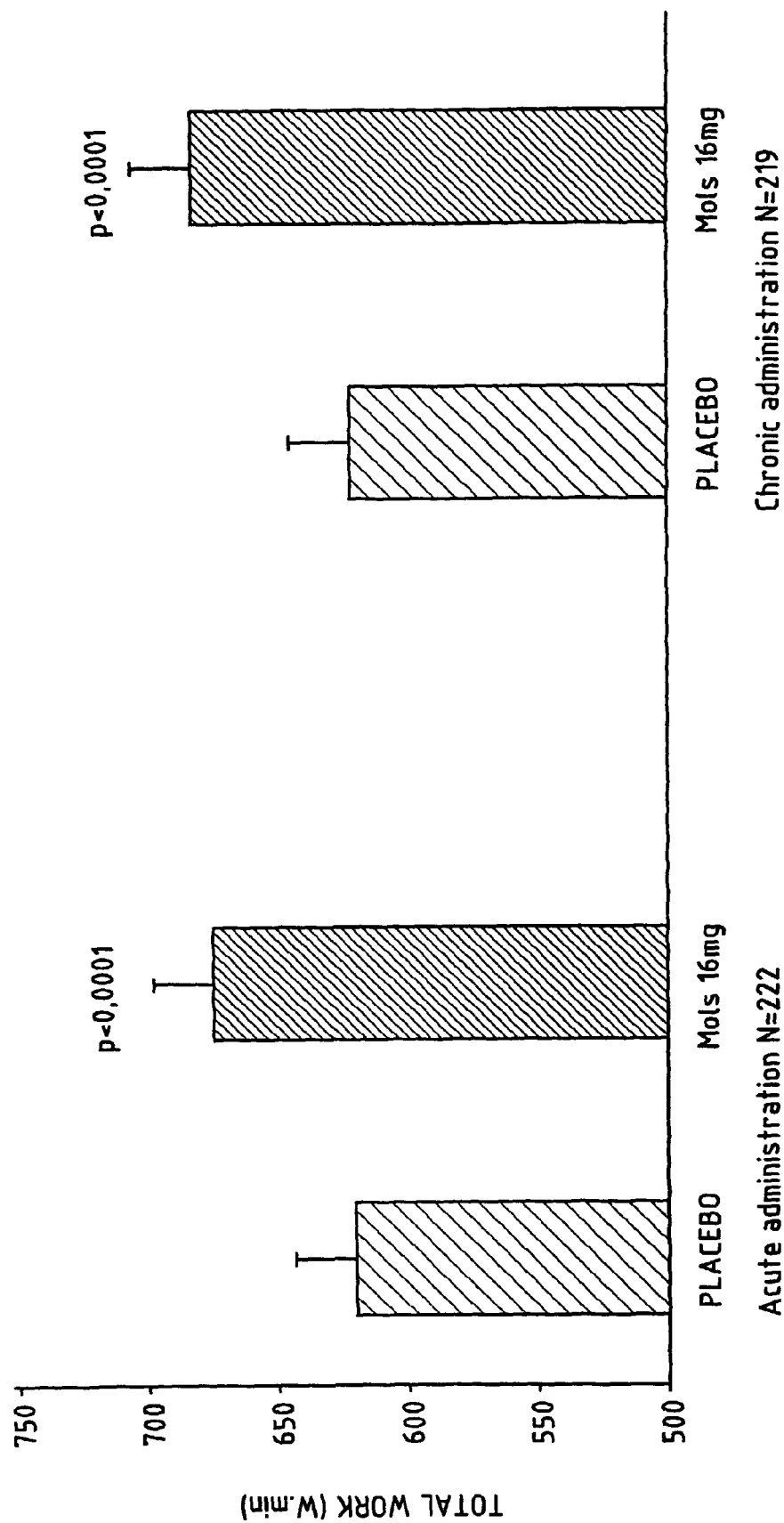

GALENICAL FORM FOR ORAL ADMINISTRATION WITH PROLONGED RELEASE OF MOLSIDOMINE

Figure 1:
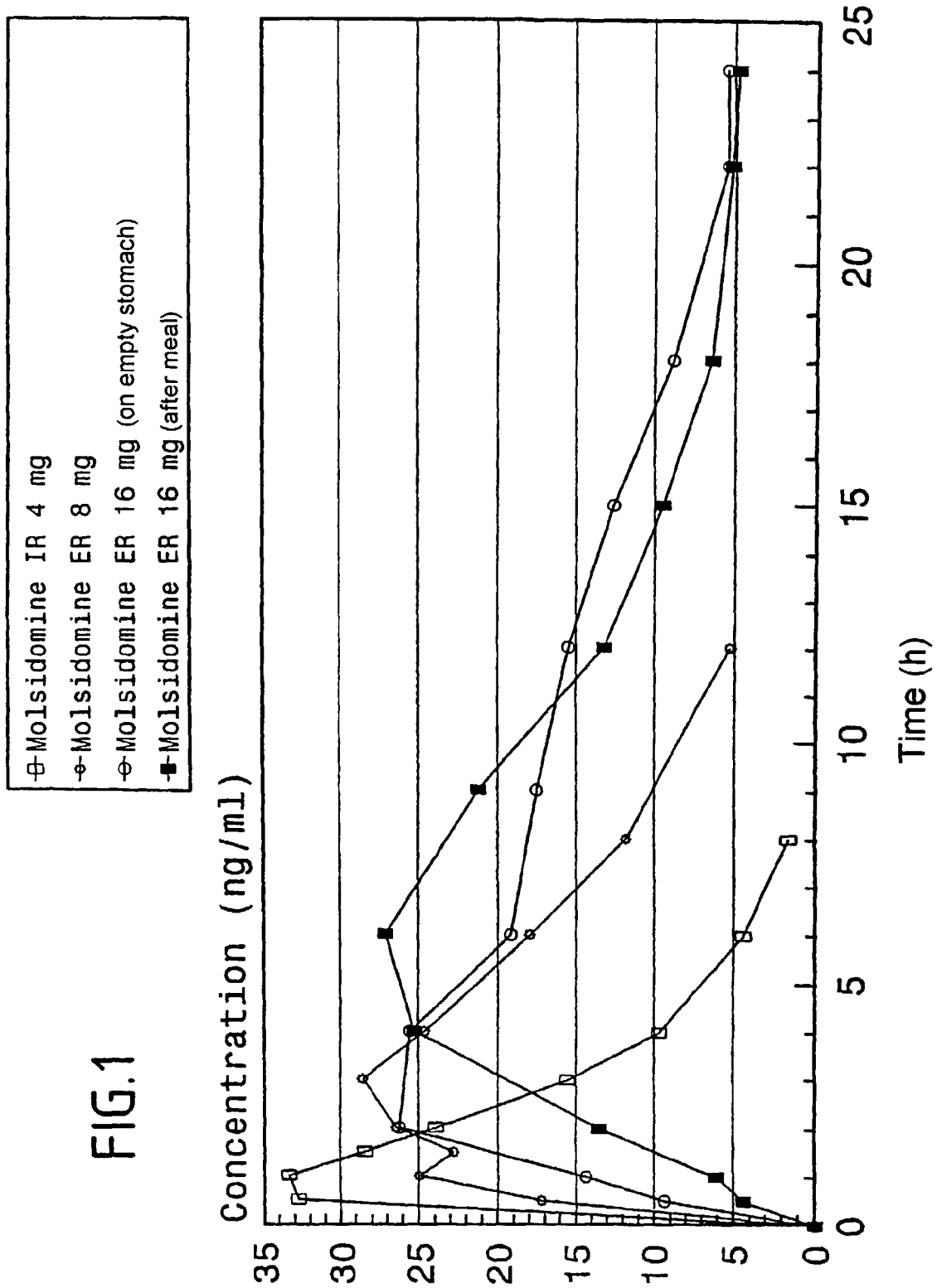

This application is a filing under 35 USC 371 of PCT/EP01/02055 filed Feb. 22, 2001.

The present invention relates to a novel sustained-release oral galenical form of molsidomine for the treatment of all forms of angina pectoris (angina of effort or rest, unstable angina).

Molsidomine (or N-(ethoxycarbonyl)-3-(4-morpholinyl) sydnone imine) is known to be the first representative of a new family of antianginals, the sydnone imines, and has been described in special drugs patent no. 6734.

This compound is particularly useful for the preventive treatment of all forms of angina attack insofar as its action causes a relaxation of the vascular smooth muscle fiber and an inhibition of the early phases of platelet activation.

The activity of this compound is attributed to its ability directly to release the NO radical during its biotransformation.

More precisely, molsidomine is a prodrug.

After oral administration, molsidomine is completely absorbed and undergoes an enzymatic transformation (hydrolysis and decarboxylation) in the liver. The SIN-1 produced is itself rapidly transformed in the blood, without enzymatic intervention, to SIN-1A. SIN-1 and SIN-1A are the active metabolites of molsidomine.

SIN-1A is then degraded by oxidation to inactive SIN-1C with the release of NO.

SIN-1C is then itself metabolized in the liver, as described in the document by Bernd Rosenkranz et al., Clinical Pharmacokinetics of Molsidomine, Clin. Pharmacokinet. 1996, May; 30 (5) 372-384.

Molsidomine is currently marketed essentially in the form of divisible tablets containing a 2 mg or 4 mg dose, which are generally administered three times a day in the treatment of angina of effort and four times a day in the treatment of angina of rest and severe angina of effort.

More recently, a new sustained-release oral galenical form of molsidomine containing an 8 mg dose, to be administered twice a day, was proposed for the long-term prophylactic treatment of angina pectoris.

In this form the maximum plasma concentration of molsidomine is observed between 1 and 3 hours after administration.

Molsidomine generally acts for a period of 4 to 5 hours for a 4 mg dose and 10 to 12 hours for an 8 mg dose.

It is generally advantageous, from the point of view of the patient's comfort, to have galenical forms with a longer therapeutic effect, since this makes it possible to reduce the number of times the drug is taken per day and thereby ensures a better patient compliance.

However, it is known in the art of pharmaceutics that prolongation of the therapeutic effect involves a significant decrease in the maximum plasma concentration and a delayed attainment of the therapeutic zone.

It has been discovered that, as regards molsidomine and its active metabolites, the therapeutic cover can be prolonged without a significant decrease in the maximum plasma concentration and with an attainment of the therapeutic zone comparable to that achieved with forms containing 4 mg or 8 mg doses; it is this discovery which forms the basis of the present invention.

Thus, although it has sustained release properties, the novel galenical form according to the invention releases a sufficient and gauged proportion of its active principle in an acid medium, i.e. mainly in the stomach, which assures a rapid attainment (about 30 min on an empty stomach to 1 h 30 min in a postprandial situation) of the therapeutic zone (5 to 10 ng/ml) and a plasma peak (33 to 40 ng/ml) equivalent to that measured with the immediate-release galenical forms.

The importance of passage through the stomach, or in other words the importance of the acid medium, could be demonstrated by means of in vivo/in vitro correlation measurements. The correlation between the percentage released in vitro and the percentage absorbed in vivo is highest, for all the forms of molsidomine, in a 0.1 N HCl medium.

Thus, according to a first feature, the present invention relates to a sustained-release solid oral galenical form of molsidomine, characterized in that it contains a therapeutically effective amount of molsidomine or one of its active metabolites, and in that it has an in vitro dissolution rate [measured spectrophotometrically at 286 or 311 nm by the method described in the European Pharmacopoeia, 3rd edition (or USP XXIV), at 50 rpm, in 500 ml of a 0.1 N HCl medium, at 37° C.] of:

15 to 25% of molsidomine released after 1 hour
20 to 35% of molsidomine released after 2 hours
50 to 65% of molsidomine released after 6 hours
75 to 95% of molsidomine released after 12 hours
>85% of molsidomine released after 18 hours
>90% of molsidomine released after 24 hours,
the plasma peak of molsidomine obtained in vivo occurring 2.5 to 5 hours, preferably 3 to 4 hours, following the administration of said form, and having a value of between 25 and 40 ng/ml of plasma.

In the present description, "the plasma peak of molsidomine obtained in vivo" corresponds to the mean maximum concentration of molsidomine found in the plasma of at least 10 healthy volunteers.

The expression "therapeutically effective amount" used within the framework of the present invention denotes a sufficient amount of molsidomine to provide a plasma concentration of at least 5 ng/mil of plasma, preferably of at least 10 ng/ml of plasma, over a period of about 24 hours.

In general, the galenical form according to the present invention can contain from 14 to 24 mg, preferably from 16 to 20 mg, of molsidomine per dosage unit, the currently preferred form containing 16 mg of molsidomine.

The expression "active metabolites" of molsidomine is intended to cover especially the compounds SIN-1 and SIN-1A resulting from the biotransformation which molsidomine undergoes after its administration.

The novel galenical form according to the invention has numerous advantages over the galenical forms of molsidomine currently on the market.

First of all, it offers a high level of patient comfort since a single daily administration is sufficient to obtain the desired therapeutic effect. This improves patient compliance.

Secondly, the maintenance of a high maximum plasma concentration guarantees an optimum efficacy during the first few hours after administration, with a very rapid attainment (30 minutes on an empty stomach and 1 h 30 min after a meal) of the therapeutic zone (5 to 10 ng/ml).

This novel galenical form therefore avoids:
on the one hand any periods during which the patient would not be protected (troughs with a concentration below 5-10 ng/ml); and
on the other hand the side effects generated through the inducement of several daily plasma peaks linked to multiple daily administrations.

Furthermore, a preliminary clinical study has shown, totally unexpectedly, that patients whose condition is stabilized by a twice daily treatment with molsidomine (sustained-release tablets containing an 8 mg dose), accompanied by the sublingual administration of organic nitro derivatives during attacks, exhibit a significant reduction in angina attacks, and consequently in the consumption of organic nitro derivatives, after treatment with a galenical form according to the invention (containing e.g. a 16 mg dose).

The novel galenical form according to the present invention can for example be in the form of tablets, in a multiparticulate form or in the form of spheroids, the tablet form being preferred.

Advantageously, the molsidomine is incorporated in a release system making it possible to obtain predefined specific in vitro dissolution rates.

This release system can consist e.g. of a sustained-release matrix or of a traditional formulation comprising a coating allowing sustained release of the molsidomine.

According to one particular characteristic of the present invention, this release system consists of an active matrix comprising, mixed with the molsidomine or one of its active metabolites, a polymeric material with a high swelling capacity in contact with water or aqueous liquids, and a gellable polymeric material, it being possible for said polymeric materials to consist of a single polymeric material having both swelling and gelling properties, said matrix optionally also containing various customary adjuvants, especially for imparting good compression characteristics thereto.

Such adjuvants are especially diluents such as lactose, lubricants such as magnesium stearate, granulating agents such as polyvinylpyrrolidone, flow improvers such as colloidal silica, and colorants such as iron oxide.

These adjuvants may be incorporated in the aforementioned matrix in an amount of between 25% and 60% by weight, based on the total weight of the matrix.

Examples of polymeric materials with a high swelling capacity which can be used within the framework of the present invention are crosslinked sodium carboxymethylcellulose, a crosslinked hydroxypropylcellulose, a high molecular weight hydroxymethylpropylcellulose, a polymethylmethacrylate, a crosslinked polyvinylpyrrolidone and a high molecular weight polyvinylalcohol.

Examples of gellable polymeric materials which can be used within the framework of the present invention are methylcellulose, carboxymethylcellulose, a low molecular weight hydroxypropylmethylcellulose, a low molecular weight polyvinylalcohol, a polyethyleneglycol and a non-crosslinked polyvinylpyrrolidone.

Within the framework of the present invention, it will be preferable to use a single polymeric material having both swelling and gelling properties. Such a material is advantageously a high molecular hydroxypropyl methyl cellulose like the product known under the trade name METHOCEL® K100M, this compound also imparting excellent viscosity properties to the final mixture.

In general, the polymeric material with a high swelling capacity and the gellable polymeric material will together represent about 40 to 60% by weight, preferably 49.0% by weight, based on the total weight of the aforementioned matrix.

The weight ratio of the polymeric material with a high swelling capacity to the gellable polymeric material can vary within wide limits.

In certain cases, to obtain the desired in vitro dissolution rates, it may be necessary to incorporate a lipophilic substance into the matrix in order to regulate the rate of release of the molsidomine.

Such a lipophilic substance is advantageously a hydrophobic lipid compound such as a hydrogenated castor oil (Cutina®), stearyl, cetostearyl or cetyl alcohol, a mono-, di- or triglyceride such as glyceryl palmitostearate or glyceryl monooleate, or solid paraffin.

Within the framework of the present invention, it will be preferable to use a glycerol behenate such as the product known under the trade name COMPRITOL® 888 ATO, this compound enabling an excellent regulation of the permeability of the matrix.

The aforementioned lipophilic substance can be present in the matrix in an amount in the region of 12% to 25% by weight, based on the total weight of the matrix.

The molsidomine release system used within the framework of the present invention can be prepared by traditional processes well known to those skilled in the art, comprising mixing, sieving, granulation, drying and compression steps.

In order to obtain the desired release profile, it can be advantageous to give the matrix a geometric shape which prolongs the release over a period of 24 hours.

Thus the release system used within the framework of the present invention can consist of a multilayer matrix comprising at least one "active" layer incorporating the molsidomine, associated with at least one "inactive" layer preferably consisting essentially of the same materials as the active layer, but not incorporating molsidomine.

In one currently preferred embodiment, the galenical form according to the present invention is that of a tablet comprising one active layer intercalated between two inactive layers.

The invention will be illustrated in greater detail by the following Examples, which are given solely by way of illustration.

EXAMPLE 1

Preparation of a Galenical Form According to the Invention as Multilayer Tablets Containing a 16 Mg Dose A galenical form according to the present invention was prepared as a tablet comprising one active layer intercalated between two inactive layers, the dimensions being as follows:

diameter of the tablet: 8.0 mm thickness of the intercalated active layer: about 2.1 mm thickness of each inactive layer: about 1.55 and 1.95 mm Each of these layers was prepared using essentially identical materials in the amounts indicated for one tablet in Table I.

TABLE I

| INGREDIENT | ACTIVE LAYER mg | INACTIVE LAYERS mg | mg |
|---|---|---|---|
| MOLSIDOMINE | 16.00 | — | — |
| METHOCEL K100M Premium | 60.00 | 39.88 | 31.90 |
| COMPRITOL 888 ATO | 20.00 | 13.50 | 10.80 |
| MANNITOL 60 | 5.00 | — | — |
| PLASDONE K29-32 | 3.70 | 5.00 | 4.00 |
| MAGNESIUM STEARATE | 1.06 | 1.00 | 0.80 |
| AEROSIL 200 | 0.44 | 0.50 | 0.40 |
| SICOVIT GELB 10 | — | 0.25 | 0.20 |
| LACTOSE PULVIS H$_2$O | — | 39.87 | 31.90 |
| TOTAL WEIGHT | 106.20 | 100.00 | 80.00 |

The active layer was prepared as follows:

The molsidomine, the polymeric material (METHOCEL® K100M), the lipophilic substance (COMPRITOL® 888 ATO), a hydrophilic filler (MANNITOL® 60) and a granulating agent (PLASDONE® K29-32) were thoroughly mixed in an appropriate mixer.

A 95% ethanol solution was prepared separately and used to moisten the powder mixture obtained above.

The resulting homogeneous mass was granulated, dried in a fluidized air bed and graded to give granules.

The resulting homogeneous granules were mixed with a flow improver (AEROSIL® 200) and a lubricant (MAGNESIUM STEARATE) and then compressed.

The inactive layers were prepared by following a protocol identical to that described above for the active layer, the pressure during the compression steps being chosen to give a perfectly homogeneous tablet (pressure of about 1000 $kg/cm^2$).

EXAMPLE 2

Determination of the in vitro Dissolution Profile of a Galenical Form According to the Invention The in vitro dissolution rate of a galenical form according to the invention, such as that prepared in Example 1, was measured using the method described in the European Pharmacopoeia, 3rd edition (or USP XXIV).

The tests were performed under the following experimental conditions:
Sotax AT7 apparatus equipped with paddles
Speed of rotation: 50 rpm
Temperature of dissolution medium: 37° C.
Filtration: Whatman GF-D filter
Assay: UV spectrophotometry at about 286 or 311 nm
Spectro: Hitachi U-3000 with 1 cm quartz cell
Dissolution medium: 500 ml of 0.1 N HCl (acid pH)
The following results were thus obtained:
18% of molsidomine released after 1 hour
27% of molsidomine released after 2 hours
57% of molsidomine released after 6 hours
88% of molsidomine released after 12 hours
96% of molsidomine released after 18 hours
100% of molsidomine released after 24 hours.

EXAMPLE 3

Comparative Study of the Principal Pharmacokinetic Characteristics of Formulations Based on Molsidomine To demonstrate the advantages and the value of the galenical form according to the present invention over the galenical forms of molsidomine known in the prior art, the principal pharmacokinetic characteristics of the following three formulations were measured:

Molsidomine-based formulation containing a 4 mg dose, corresponding to the product currently marketed in Belgium under the name CORVATON® 4 mg.

Molsidomine-based formulation containing an 8 mg dose, currently marketed in Belgium under the name CORVATARD®.

Formulation according to the present invention containing a 16 mg dose (prepared according to Example 1).

The different parameters below were measured for each of these formulations using experimental protocols well known to those skilled in the art:
Cmax: maximum plasma concentration
Tmax: time for which Cmax is observed
AUC 0-t: area under the curve between time 0 and time t
T½: elimination half-life
MRT: mean residence time of the substance in the organism In the case of the formulation according to the present invention, these pharmacokinetic characteristics were determined on young healthy volunteers on an empty stomach and then after a meal.

The results obtained have been collated in Table II.

TABLE II

|  | MOLSIDOMINE 4 mg (n = 12) | MOLSIDOMINE 8 mg (n = 12) | MOLSIDOMINE 16 mg (empty stomach) (n = 10) | MOLSIDOMINE 16 mg (meal) (n = 10) |
|---|---|---|---|---|
| Cmax (ng/ml) | 40.13 ± 19.03 | 33.80 ± 15.44 | 34.19 ± 25.37 | 34.76 ± 15.03 |
| Tmax (h) | 0.75 ± 0.34 | 1.67 ± 0.94 | 3.00 ± 1.41 | 4.60 ± 2.10 |
| AUC 0-t (ng · h/ml) | 103.6 ± 79.40 | 195.5 ± 124.5 | 372.5 ± 278.1 | 327.7 ± 166.9 |
| AUC 0-∞ (ng · h/ml) | 114.8 ± 89.40 | 229.8 ± 154.4 | 527.2 ± 466.6 | 409.3 ± 194.1 |
| T½ (h) | 1.55 ± 0.50 | 3.35 ± 0.78 | 11.87 ± 10.35 | 11.54 ± 10.21 |
| MRT (h) | 2.64 ± 0.74 | 5.81 ± 1.47 | 18.99 ± 11.84 | 17.58 ± 11.33 |

Also, the change in the plasma concentration as a function of time for each of the formulations studied has been shown in FIG. 1.

The results obtained show that the formulation containing a 4 mg dose provides a plasma concentration for about 4 to 5 hours, the formulation containing an 8 mg dose provides a plasma concentration for about 10 to 12 hours and the formulation according to the invention containing a 16 mg dose provides a plasma concentration for about 24 hours.

It can be seen that the maximum plasma concentration is more or less equivalent for the three formulations and is between 33 and 40 ng/ml.

The result obtained with the formulation according to the present invention is totally unexpected since the prolongation of the therapeutic effect does not entail a significant decrease in the Cmax. There is no statistically significant difference between the galenical form according to the present invention and the traditional forms (ANOVA followed by Bonferonni post-hoc tests).

These results also show that the formulation according to the invention guarantees an efficacy comparable to that of the known formulations, even during the first few hours after administration, with a rapid attainment of the therapeutic zone within about 30 min (on an empty stomach) or 90 min (after a meal).

EXAMPLE 4

Comparative Study of the Correlations Between the in vitro Release Kinetics in Different Media and the in vivo Absorption Kinetics

| In vivo - in vitro correlation | Molsidomine 4 mg | Molsidomine 8 mg | Molsidomine 16 mg (empty stomach) | Molsidomine 16 mg (meal) |
|---|---|---|---|---|
| at pH 6.8 | 0.958 | 0.835 | 0.712 | 0.761 |
| at acid pH (0.1 N HCl medium) | 0.877 | 0.855 | 0.748 | 0.812 |
| pH dependence* | NA | 0.817 | 0.719 | 0.755 |

NA = not applicable
*Note:
The term "pH dependence" denotes that, during the in vitro dissolution test, the tablets tested are kept:
at pH 1.3 for 1 hour
at pH 5.0 for 30 minutes
at pH 6.3 for 3 hours
at pH 7.0 for the remainder of the time All the correlation coefficients are significant ($p<0.01$; Pearson's test). The best correlation (0.958) is obtained with the immediate form (molsidomine 4 mg), which seems fairly logical. In fact, it is known that the more complex a galenical form is, the more difficult it is to find a correlation between in vitro release and in vivo absorption. For molsidomine 8 mg, the correlation is still very high (0.855). For molsidomine 16 mg, the correlation is best (0.812) when the postprandial kinetics and the dissolution in an acid medium are taken into account. In general terms, for the sustained-release forms, the correlations are always better when the release is carried out in an acid medium. This is explained by the fact that a large part of the kinetics of molsidomine depends on the gastric absorption.

EXAMPLE 5

Study of the Plasma Concentration Resulting from the Administration of a Molsidomine Formulation According to the Invention, as a Function of Time, in Elderly Angina Patients Thirty-three coronary patients suffering from stable angina pectoris received a single dose of molsidomine 16 mg (formulation according to Example 1) with breakfast at 8 am. They comprised 22 men and 11 women with an average age of 62.6±1.3 years (extreme values: 49 to 73 years). The patients were divided into 7 groups and blood samples were taken respectively 3, 6, 10, 14, 18, 22 and 24 hours after ingestion of the drug for determination of the molsidomine.

Figure 2:
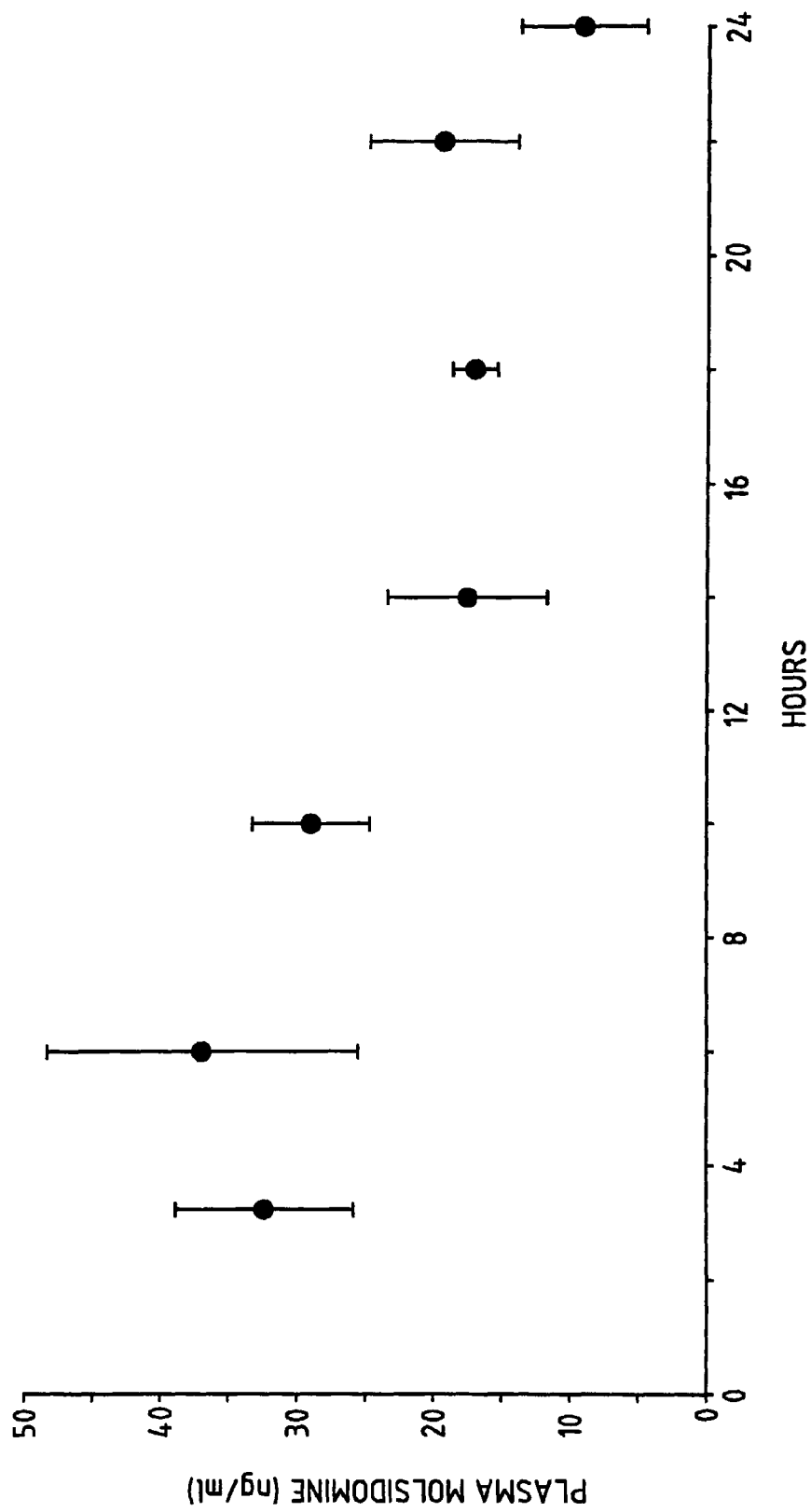

FIG. 2 shows the mean plasma concentration of molsidomine and its standard error for each of the 7 groups of patients studied.

As shown in this Figure, the kinetics profile observed in elderly patients correlates very well with that observed in young healthy volunteers (shown in FIG. 1). Furthermore, the Cmax, Tmax and half-life values are comparable.

It is also found that:
the maximum mean concentration is 36.0±10.8 ng/ml;
the highest mean concentration is observed in group 2, i.e. 6 hours after ingestion of the molsidomine;
the concentration decreases slowly, namely by 50% in 8 hours;
the plasma concentration of molsidomine remains on a plateau for 8 hours, namely from +14 to +22 hours after administration, the mean value fluctuating between 16.5 and 18.1 ng/ml;
a residual concentration of 8.5±4.3 ng/ml is still observed 24 hours after the administration of a single dose of molsidomine 16 mg.

EXAMPLE 6

Study of the Correlation Between the Clinical Efficacy and the Plasma Concentration of a Molsidomine Formulation According to the Invention Ten coronary patients suffering from stable angina pectoris were deprived of all antianginal treatment (sustained-action nitro derivatives, molsidomine, calcium antagonists and/or beta-blockers) for a minimum period of 3 days, or longer in the case of those taking beta-blockers; during this period they were only allowed to take isosorbide dinitrate 5 mg sublingual tablets or to use a nitroglycerin spray.

These patients then received a single dose of molsidomine 16 mg (formulation according to Example 1) or placebo according to a crossed double-blind randomization technique including a deprivation period of at least 2 full days.

The patients comprised 8 men and 2 women with an average age of 61.3±3.1 years (extreme values: 49 to 73).

The patients were divided into 7 groups and blood samples were taken respectively 3, 6, 10, 14, 18, 22 and 24 hours after ingestion of the drug or placebo for determination of the molsidomine after a stress test on a cyclo-ergometer.

The stress test comprised an initial load of 30 Watts with an increase of 30 Watts every 3 minutes to the end of the test for angina symptoms, attainment of the theoretical maximum heart rate, or muscle fatigue, or for safety reasons (intracardiac conduction or rhythm disorder, drop in blood pressure >20 mmHg, depression of segment $ST \geq 3$ mm); the ECG and the arterial pressure were recorded at rest and throughout the stress test.

The clinical efficacy of the formulation according to the invention was quantified by:
a) the difference in total exercise time, expressed in seconds, under placebo and under molsidomine;
b) the difference in total work performed, expressed as the sum of the products Watts×min calculated for each stress level, under placebo and under molsidomine.

Figure 3:
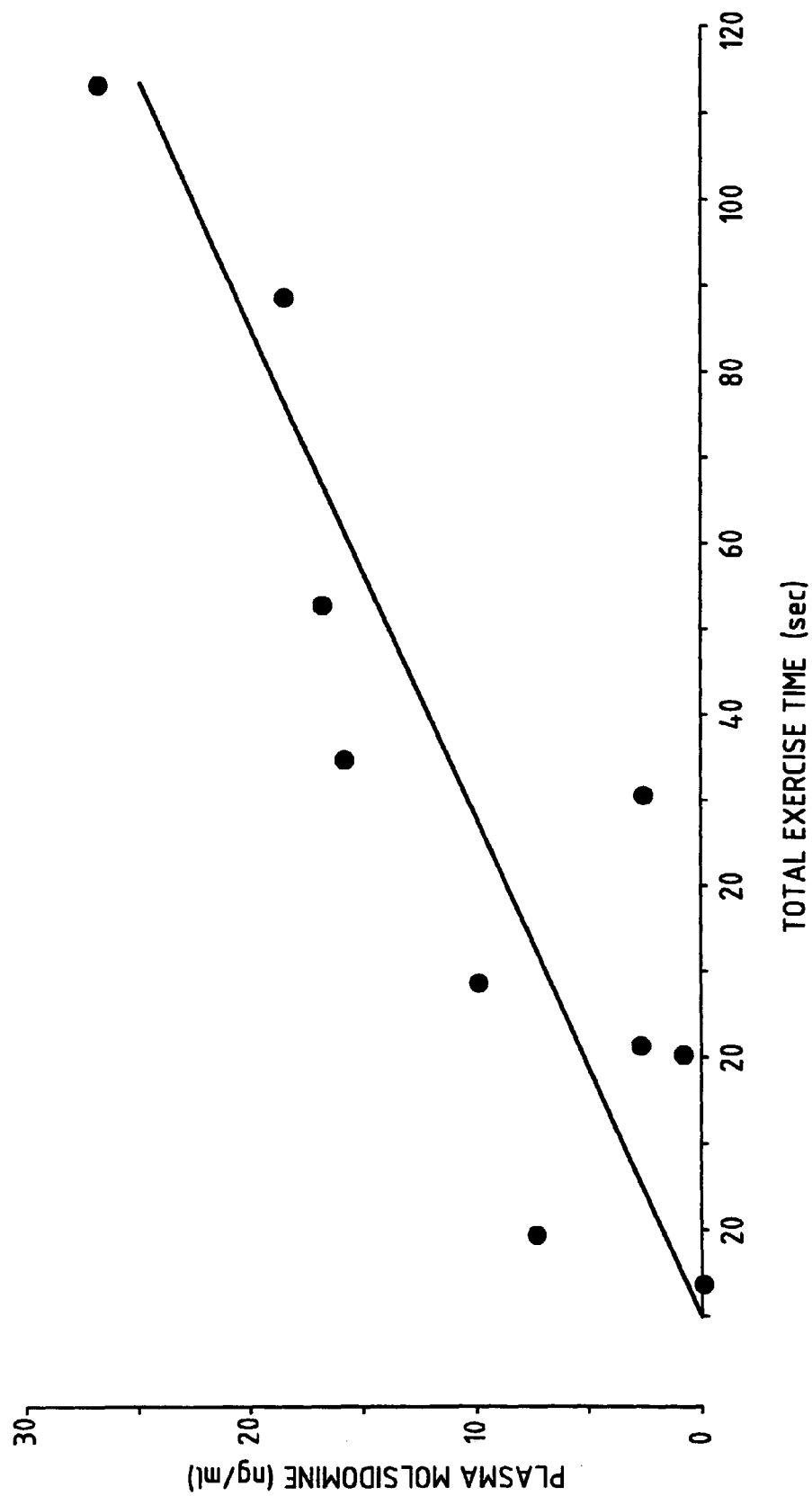

FIG. 3 shows the plasma concentrations of molsidomine observed in each of the 10 patients and the corresponding differences in total exercise time.

The equation of the regression line between the variable X (difference between the total exercise time under placebo and under molsidomine) and the variable Y (plasma concentration of molsidomine) is: $Y = 0.18\,X + 5.35$.

The Pearson correlation coefficient r is 0.88 ($P<0.001$), which corresponds to a coefficient of determination $r^2$ of 0.77, it being possible to explain 77% of the variance in clinical efficacy by the plasma concentration of molsidomine.

A quadratic or cubic model does not improve the correlation coefficient.

If a difference of 30 seconds between stress tests performed under placebo and molsidomine is considered to be clinically significant, it appears that the plasma concentration of molsidomine required for this level of efficacy is 10.75 ng/ml, a value which is still attained in practice 24 hours after a single administration of molsidomine 16 mg according to the invention (cf. FIG. 2).

Figure 4:
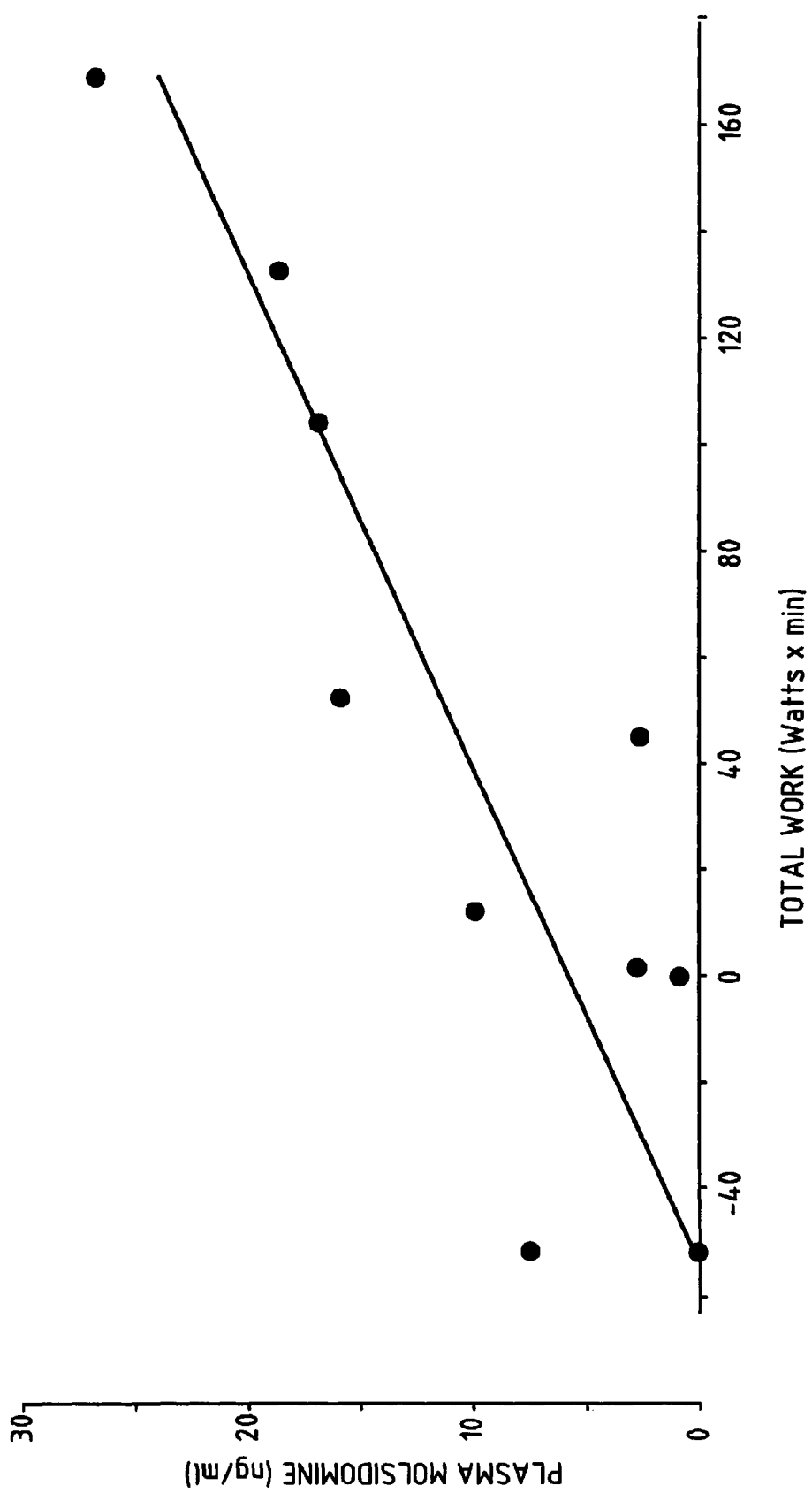

FIG. 4 shows the plasma concentrations of molsidomine observed in each of the 10 patients and the corresponding differences in total work performed.

The equation of the regression line between the variable X (difference between the total work performed under placebo and under molsidomine) and the variable Y (plasma concentration of molsidomine) is: Y=0.11 X+5.90.

The Pearson correlation coefficient r is 0.86 (p=0.002), which corresponds to a coefficient of determination $r^2$ of 0.74, it being possible to explain 74% of the variance in clinical efficacy by the plasma concentration of molsidomine.

A quadratic or cubic model does not improve the correlation coefficient.

If a difference of 50 Watts×min between stress tests performed under placebo and molsidomine is considered to be clinically significant, it appears that the plasma concentration of molsidomine required for this level of efficacy is 11.40 ng/ml, a value which is still attained in practice 24 hours after a single administration of molsidomine 16 mg according to the invention (cf. FIG. 2).

EXAMPLE 7

Study of the Clinical Efficacy of a Molsidomine Formulation According to the Invention Two hundred and twenty-two patients suffering from stable angina of effort participated in a placebo-controlled, double-blind, randomized, multicenter multinational study.

After the administration of a single dose of molsidomine 16 mg (formulation according to Example 1) or placebo, they underwent a stress test on a cyclo-ergometer within 2 h to 24 h after taking the drug. The stress capacity (total work performed, expressed in Watts×min) is significantly higher under molsidomine than under placebo, both statistically (p<0.001) and clinically (mean improvement of 53 Watts×min).

The administration of the same single daily dose of molsidomine 16 mg (formulation according to Example 1) for 2 weeks results in an improvement in physical performance comparable to that observed after acute administration and significant both statistically (p<0.001) and clinically (mean improvement of 58 Watts×min).

These results demonstrate the absence of habituation to molsidomine 16 mg after prolonged treatment (FIG. 5). They also indicate that the therapeutic efficacy extends over 24 hours.

It will be noted that the clinical improvements observed in this study are in perfect agreement with the clinically effective plasma concentrations of molsidomine deduced from the total work/plasma molsidomine correlation shown in FIG. 4.

The results obtained in Examples 5, 6 and 7 above demonstrate the originality of the novel galenical form of molsidomine according to the invention.

The main advantages of this form over the existing forms can be summarized as follows:
  maintenance of a high plateau of plasma molsidomine concentration (16.5 to 18.1 ng/ml) for 8 hours (from +14 hours to +22 hours after ingestion of the drug);
  plateau of plasma concentration which ensures a significant clinical efficacy in coronary patients with stable angina pectoris, as demonstrated by the close correlation between the increase in stress capacity and the blood molsidomine concentration, an improvement which is maintained for 24 hours after administration of the drug;
  absence of habituation to molsidomine, a significant clinical efficacy persisting after 2 weeks of treatment in coronary patients with stable angina pectoris.

The invention claimed is:

1. A sustained-release solid oral galenical form of molsidomine which contains a sustained-release matrix containing a therapeutically effective amount of molsidomine or one active metabolite of molsidomine selected from the group consisting of SIN-1 and SIN-1A,
  said matrix consisting essentially of:
    at least 40% by weight of a material selected from the group consisting of:
      a polymeric material having a high swelling capacity in contact with water or aqueous liquids and gelling properties, and which is a high molecular weight hydroxypropyl methyl cellulose; and
      a mixture of a polymeric material having a high swelling capacity in contact with water or aqueous liquids selected from the group consisting of crosslinked sodium carboxymethylcellulose, a crosslinked hydroxypropylcellulose, a high molecular weight hydroxymethylpropylcellulose, a polymethylmethacrylate, a crosslinked polyvinylpyrrolidone and a high molecular weight polyvinylalcohol, and a gellable polymeric material selected from the group consisting of methylcellulose, carboxymethylcellulose, a low molecular weight hydroxypropylmethylcellulose, a low molecular weight polyvinylalcohol, a polyethyleneglycol and a non-crosslinked polyvinylpyrrolidone;
    between 12% and 25% by weight of a lipophilic substance selected from the group consisting of glycerol behenate, an hydrogenated castor oil, glyceryl palmitostearate and glyceryl monooleate; and
    at least 25% by weight of at least one adjuvant selected from the group consisting of diluents, lubricants, granulating agents, flow improvers and colorants;
    said galenic form having an in vitro dissolution rate, measured spectrophotometrically at 286 or 311 nm by the method described in the European Pharmacopoeia, 3rd edition or by the method USP XXIV, at 50 rpm, in 500 ml of a 0.1 N HCl medium, at 37° C. of:
    15 to 25% of molsidomine released after 1 hour
    20 to 35% of molsidomine released after 2 hours
    50 to 65% of molsidomine released after 6 hours
    75 to 95% of molsidomine released after 12 hours
    >85% of molsidomine released after 18 hours
    >90% of molsidomine released after 24 hours,
  and providing a plasma concentration of at least 5 ng/ml of plasma, over a period of about 24 hours,
  the plasma peak of molsidomine obtained in vivo occurring 2.5 to 5 hours following the administration of said form, and having a value of between 25 and 40 ng/ml of plasma.

2. A galenical form according to claim 1, which comprises from 14 to 24 mg of molsidomine.

3. A galenical form according to claim 1, which comprises from 16 to 20 mg of molsidomine.

4. A galenical form according to claim 1, which comprises 16 mg of molsidomine and provides a plasma concentration of at least 10 ng/ml of plasma, over a period of 24 hours.

5. A galenical form according to claim 1, which is in a form selected from the group consisting of tablets, multiparticulate form and spheroids.

6. A galenical form according to claim 1, wherein said matrix consists essentially of:
- at least 40% by weight of a high molecular weight hydroxypropyl methyl cellulose;
- between 12% and 25% by weight of glycerol behenate; and
- at least 25% by weight of at least one adjuvant selected from the group consisting of diluents, lubricants, granulating agents, flow improvers and colorants.

7. A galenical form according to claim 1, which is in the form of multilayer tablets comprising an active layer incorporating the molsidomine, associated with at least one inactive layer which does not incorporate molsidomine.

8. A galenical form according to claim 7, wherein said inactive layer contains the same materials as the active layer, but does not include molsidomine.

9. A galenical form according to claim 7, which consists essentially of one active layer intercalated between two inactive layers.

10. A sustained-release solid oral galenical form of molsidomine which contains a sustained-release matrix containing a therapeutically effective amount of molsidomine or one active metabolite of molsidomine selected from the group consisting of SIN-1 and SIN-1A,
said matrix consisting essetially of:
- at least 40% by weight of a high molecular weight hydroxypropyl methyl cellulose;
- between 12 and 25% by weight of glycerol behenate; and
- at least 25% by weight of at least one adjuvant selected from the group consisting of diluents, lubricants, granulating agents, flow improvers and colorants;
said galenic form having an in vitro dissolution rate, measured spectrophotometrically at 286 or 311 nm by the method described in the European Pharmacopoeia, 3rd edition or by the method USP XXIV, at 50 rpm, in 500 ml of a 0.1 N HCl medium, at 37° C. of:
- 15 to 25% of molsidomine released after 1 hour
- 20 to 35% of molsidomine released after 2 hours
- 50 to 65% of molsidomine released after 6 hours
- 75 to 95% of molsidomine released after 12 hours
- >85% of molsidomine released after 18 hours
- >90% of molsidomine released after 24 hours,
and providing a plasma concentration of at least 5 ng/ml of plasma, over a period of about 24 hours,
the plasma peak of molsidomine obtained in vivo occurring 2.5 to 5 hours following the administration of said form, and having a value of between 25 and 40 ng/ml of plasma.

11. A galenical form according to claim 10, which comprises from 14 to 24 mg of molsidomine.

12. A galenical form according to claim 10, which comprises from 16 to 20 mg of molsidomine.

13. A galenical form according to claim 10, which comprises 16 mg of molsidomine and provides a plasma concentration of at least 10 ng/ml of plasma, over a period of 24 hours.

14. A galenical form according to claim 10, which is in a form selected from the group consisting of tablets, multiparticulate form and spheroids.

15. A galenical form according to claim 10, which is in the form of multilayer tablets comprising an active layer incorporating the molsidomine, associated with at least one inactive layer which does not incorporate molsidomine.

16. A galenical form according to claim 15, wherein said inactive layer consists of the same materials as the active layer, but does not include molsidomine.

17. A galenical form according to claim 15, which consists of one active layer intercalated between two inactive layers.

* * * * *